United States Patent
Chen et al.

(10) Patent No.: US 12,202,793 B2
(45) Date of Patent: Jan. 21, 2025

(54) PROCESS FOR CONVERTING METHANOL TO FORMALDEHYDE

(71) Applicant: CELANESE INTERNATIONAL CORPORATION, Irving, TX (US)

(72) Inventors: Wensheng Chen, Friendswood, TX (US); Justin Dodson, League City, TX (US); Steve Alexander, Houston, TX (US); Monty Sinnreich, Corpus Christi, TX (US); Randal Jendrzey, Corpus Christi, TX (US)

(73) Assignee: Celanese International Corporation, Irving, TX (US)

( * ) Notice: Subject to any disclaimer, the term of this patent is extended or adjusted under 35 U.S.C. 154(b) by 296 days.

(21) Appl. No.: 17/773,961

(22) PCT Filed: Nov. 12, 2020

(86) PCT No.: PCT/US2020/060128
§ 371 (c)(1),
(2) Date: May 3, 2022

(87) PCT Pub. No.: WO2021/097023
PCT Pub. Date: May 20, 2021

(65) Prior Publication Data
US 2022/0388936 A1   Dec. 8, 2022

Related U.S. Application Data

(60) Provisional application No. 62/935,713, filed on Nov. 15, 2019.

(51) Int. Cl.
*C07C 45/51*   (2006.01)
*B01J 8/04*    (2006.01)
*B01J 23/50*   (2006.01)
*C07C 45/38*   (2006.01)
*C07C 47/04*   (2006.01)

(52) U.S. Cl.
CPC ............. *C07C 47/04* (2013.01); *B01J 8/0492* (2013.01); *B01J 23/50* (2013.01); *C07C 45/38* (2013.01); *C07C 45/512* (2013.01)

(58) Field of Classification Search
CPC ........ C07C 45/512; C07C 45/38; C07C 47/04
See application file for complete search history.

(56) References Cited

U.S. PATENT DOCUMENTS

| | | |
|---|---|---|
| 4,076,754 A | 2/1978 | Kiser et al. |
| 4,219,509 A | 8/1980 | Nielsen et al. |
| 4,424,397 A | 1/1984 | Hoene et al. |
| 2020/0009535 A1* | 1/2020 | Troussard ................ B01J 37/14 |

FOREIGN PATENT DOCUMENTS

| | | |
|---|---|---|
| DE | 1231229 B | 12/1966 |
| DE | 1294360 B | 5/1969 |
| WO | 2018153736 A1 | 8/2018 |

OTHER PUBLICATIONS

Written Opinion and International Search Report of PCT/US2020/060128 mailed Feb. 25, 2021.

* cited by examiner

*Primary Examiner* — Sikarl A Witherspoon
(74) *Attorney, Agent, or Firm* — Kilpatrick Townsend & Stockton LLP

(57) ABSTRACT

A method for catalytic vapor phase oxidation of methanol to formaldehyde may include: passing a feed stream comprising methanol and oxygen through a layered catalyst bed having a first layer comprising a first silver catalyst particles and a second layer comprising a second silver catalyst particles that are different than the first silver catalyst particles, wherein the feed stream passes through the first layer before the second layer, wherein the first silver catalyst particles has a greater reaction activity for converting methanol and oxygen to formaldehyde; and reacting the methanol and the oxygen in the presence of the catalysts to produce a product stream comprising formaldehyde.

23 Claims, 3 Drawing Sheets

PROCESS FOR CONVERTING METHANOL TO FORMALDEHYDE

BACKGROUND

The present disclosure relates to catalytic vapor phase oxidation of methanol to formaldehyde.

Formaldehyde is one of the most important commodity chemicals and is used in the production of various resins and polymers. Formaldehyde can be synthesized by partial oxidation of methanol in the presence of a catalyst, typically, a silver metal catalyst or a metal oxide catalyst. Said reaction is exothermic, and at higher temperatures, the formaldehyde product can decompose and deposit carbon (coke) on catalyst particles. So, catalyst composition and catalyst bed configuration have been used to mitigate hot spots prone to coking while maintaining a high formaldehyde yield.

In one example, a silver catalyst particles having a broad range of sizes is used. Generally, smaller catalyst particles have a slightly higher reaction activity. In this catalyst bed configuration, the smaller particles are dispersed homogeneously so that hot spots that are prone to coking are mitigated. In another example, silver catalyst particles having the crystal structure composition are sieved and layered so that the larger diameter particles are near the outlet and contact the reactants after the smaller particles. However, both catalyst bed designs are prone to coking because the large and small particles have a similarly high reaction activity and the downstream particles decompose the formaldehyde.

SUMMARY OF INVENTION

The present disclosure relates to catalytic vapor phase oxidation of methanol to formaldehyde. More specifically, the present disclosure relates to the composition and configuration of the catalyst bed for said reaction where silver catalysts of different crystal structures are used such that the silver catalyst particles with higher reaction activity are encountered first by the feed stream.

The present disclosure includes a method comprising: passing a feed stream comprising methanol and oxygen through a layered catalyst bed having a first layer comprising a first silver catalyst particles and a second layer comprising a second silver catalyst particles that are different than the first silver catalyst particles, wherein the feed stream passes through the first layer before the second layer, wherein the first silver catalyst particles has a greater reaction activity for converting methanol and oxygen to formaldehyde; and reacting the methanol and the oxygen in the presence of the catalysts to produce a product stream comprising formaldehyde.

Said first silver catalyst particles may be characterized by one or more of: (a) wherein the first silver catalyst particles have a dendritic morphology; (b) wherein the first silver catalyst particles have an x-ray diffraction pattern characterized by having a (1 1 1) Miller index intensity greater than an intensity of each of the following Miller indices: (2 0 0), (2 2 0), (3 1 1), (2 2 2), (4 0 0), (3 3 1), (4 2 0), and (1 1 0); (c) wherein the first silver catalyst particles have an x-ray diffraction pattern characterized by having a (1 1 1):(2 2 0) Miller indices intensity ratio of about 1:1 to about 3.5:1; and (d) wherein the first silver catalyst particles have an x-ray diffraction pattern characterized by having a (1 1 1):(1 1 0) Miller indices intensity ratio of about 1.5:1 or greater.

Said second silver catalyst particles may be characterized by one or more of: (a) wherein the second silver catalyst particles have an x-ray diffraction pattern characterized by having a (1 1 1) Miller index intensity less than an intensity of one or more of the following Miller indices: (2 0 0), (2 2 0), (3 1 1), (2 2 2), (4 0 0), (3 3 1), (4 2 0), and (1 1 0); (b) wherein the second silver catalyst particles have an x-ray diffraction pattern characterized by having ratio of a (1 1 1) Miller index intensity to an intensity of a largest intensity peak between 30 degrees 2 theta angle and 120 degrees range 2 theta angle of 0.7 or less; and (c) wherein the second silver catalyst particles have an x-ray diffraction pattern characterized by having a (1 1 1):(2 2 0) Miller indices ratio of about 0.05:1 to about 0.8:1.

Said first and second silver catalyst particles may be characterized by one or more of:

(a) wherein the first silver catalyst particles has a purity of about 98% to about 99.5%, and wherein the second silver catalyst particles has a purity of about 85% to about 99%, where the purity of the first silver catalyst particles is greater than the purity of the second silver catalyst particles; (b) wherein one or both of the first and second silver catalyst particles comprises about 5 wt % to about 80 wt % of one or more alloy metals and about 20 wt % to about 95 wt % silver; (c) wherein the first silver catalyst particles have sieved particle sizes ranging from about 0.25 mm to about 4 mm, and the second silver catalyst particles have sieved particle sizes ranging from about 0.5 mm to about 4 mm, wherein the first silver catalyst particles are sieved to include particles smaller than included in the second silver catalyst particles; (d) wherein the first silver catalyst particles have an apparent bulk density of about 3 g/mL or less, wherein the second silver catalyst particles have an apparent bulk density of about 3 g/mL or greater, and wherein the apparent bulk density of the first silver catalyst particles is smaller than the apparent bulk density of the second silver catalyst particles; and (e) wherein the first silver catalyst particles have an oxygen desorption temperature of about 220° C. to about 270° C., wherein the second silver catalyst particles have an oxygen desorption temperature of about 270° C. to about 310° C., and wherein the oxygen desorption temperature of the first silver catalyst particles is smaller than the oxygen desorption temperature of the second silver catalyst particles.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to catalytic vapor phase oxidation of methanol to formaldehyde. More specifically, the present disclosure relates to the composition and configuration of the catalyst bed for said reaction.

The present disclosure uses a layered catalyst bed where the silver catalyst particles are first contacted by the reactants and where the majority, if not all, of the formaldehyde production occurs. The second silver catalyst particles contacted has less reactivity, to minimize formaldehyde decomposition and coking (or fouling), and acts primarily as a heat transfer medium. Further, because the silver catalyst particles having a higher reaction activity are encountered first, the catalyst bed can be operated at a lower temperature. Lower operating temperature reduces the coke production and catalyst bed fouling, thereby lengthening the lifetime of the catalyst bed. Further, lower operating temperatures allow for a lower time to achieve operating conditions.

The differences in reactivity between the silver catalyst particles in the two layers is achieved with different compositions of catalysts. Generally, each of the silver catalyst particles are polycrystalline, where the more reactive silver catalysts have more (1 1 1) crystallinity than the less reactive silver catalyst. Silver is a metal with a very high thermal diffusivity, so by controlling the reactivity of two silver catalyst particles through crystal structure, the advantages of silver's high thermal diffusivity and reactivity for the methanol to formaldehyde reaction can both be exploited.

Methods

Methods of the present disclosure include passing a feed stream comprising methanol and oxygen through a layered catalyst bed having a first layer comprising first silver catalyst particles and a second layer comprising second silver catalyst particles that are different than the first silver catalyst particles, wherein the feed stream passes through the first layer before the second layer, wherein the first silver catalyst particles has a greater reaction activity for converting methanol and oxygen to formaldehyde; and reacting the methanol and the oxygen in the presence of the catalysts to produce a product stream comprising formaldehyde. The product stream may then be cooled and purified or otherwise treated to achieve a desired formaldehyde product. The catalyst activity can be quantified by either catalyst light off time under identical reaction conditions or a threshold temperature above which the reaction takes place. The higher the catalyst activity, the shorter is the catalyst light off time and lower the reaction threshold temperature.

Figure 1:
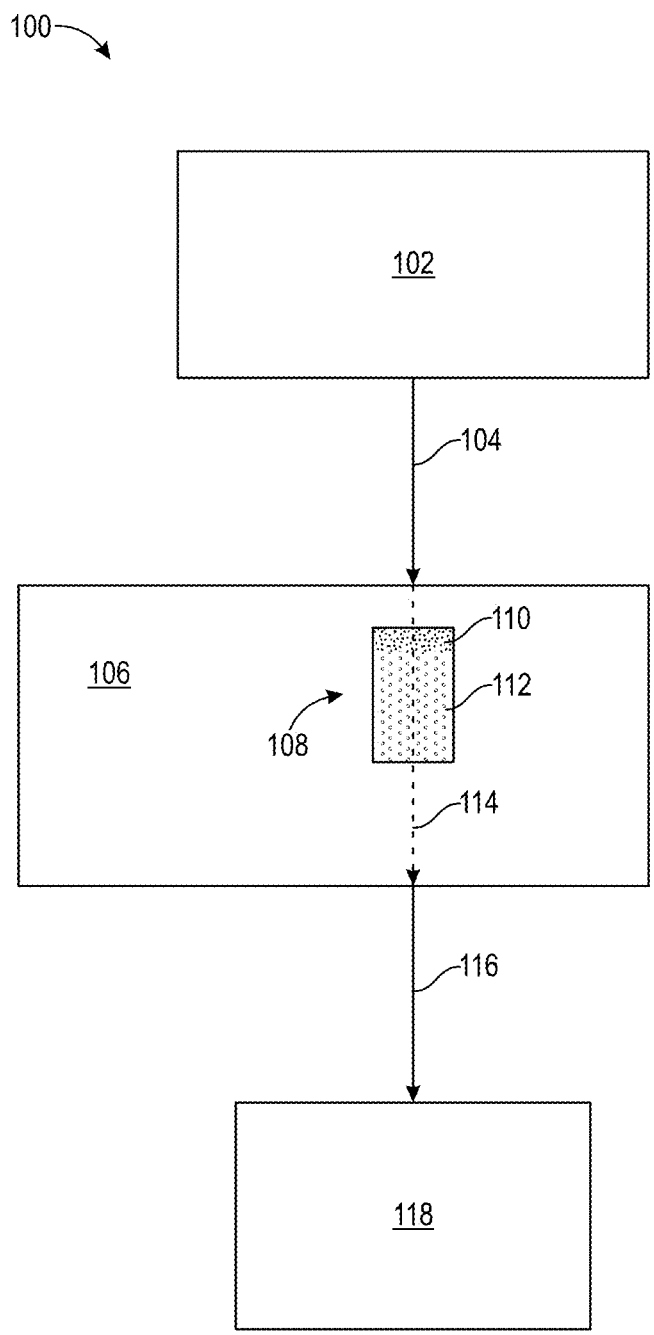
FIG. 1 is an illustrative diagram of a nonlimiting example of a method of the present disclosure.

FIG. 1 is an illustrative diagram of a nonlimiting example of a method 100 of the present disclosure. The method comprises feeding 104 a feed stream 102 comprising methanol and oxygen to a reactor 106 comprising a layered catalyst bed 108. The layered catalyst bed 108 comprises a first layer 110 comprising first silver catalyst particles and a second layer 112 comprising second silver catalyst particles that are different from the first silver catalyst particles. In the layered catalyst bed 108, the methanol and oxygen react to form formaldehyde, which is in the product stream 114. The product stream 114 is then treated 116 (e.g., cooled, purified, and the like) to produce a formaldehyde product 118 having a desired purity and composition.

FIG. 1 generally outlines a nonlimiting example method 100. Other streams and/or equipment can be used per known methods in the art for formaldehyde production. For example, an inert gas stream may be recovered in the treating 116 step(s) and optionally recycled back to the feed stream 102. In another example, the reactor 106 may be configured for one-stage methanol conversion to formaldehyde or two-stage methanol conversion to formaldehyde. In a two-stage methanol conversion to formaldehyde, the first stage may utilize a layered catalyst bed described herein, the second stage may utilize a layered catalyst bed described herein, or both the first and second stages may utilize layered catalyst beds described herein. One skilled in the art will recognize how to adapt a known variation of formaldehyde production from methanol to incorporate the layered catalyst bed 108 described herein.

The feed stream 102 may comprise, by volume, about 15% to about 43% (or about 15% to about 30%, or about 25% to about 43%) methanol, about 5% to about 15% (or about 5% to about 10%, or about 10% to about 15%) oxygen, about 35% to about 50% (or about 35% to about 45%, or about 40% to about 50%) inert gas (e.g., nitrogen and/or argon), 0% to 30% (or about 0% to about 5%, or about 0% to about 20%, or about 15% to about 30%) formaldehyde, and about 9% to about 30% (or about 9% to about 20%, or about 15% to about 30%) water.

Generally, the feed stream 102 is preheated to a temperature of about 90° C. to about 170° C., or about 90° C. to about 125° C., or about 120° C. to about 170° C.

The first layer may comprise the first silver catalyst particles at about 75 wt % to about 100 wt %, or about 85 wt % to about 100 wt %, or about 75 wt % to about 99 wt %, or about 85 wt % to about 99 wt %, or about 95 wt % to about 99 wt % of the first layer. The first layer may consist of the first silver catalyst particles.

The second layer may comprise the second silver catalyst particles at about 75 wt % to about 100 wt %, or about 85 wt % to about 100 wt %, or about 75 wt % to about 99 wt %, or about 85 wt % to about 99 wt %, or about 95 wt % to about 99 wt % of the second layer. The second layer may consist of the second silver catalyst particles.

Within the reactor, the weight ratio of the first layer 110 to the second layer 112 may be about 0.01:1 to about 0.5:1, or about 0.01:1 to about 0.25:1, or about 0.01:1 to about 0.15:1.

Layering of the first and second layers 110, 112 in the layered catalyst bed 108 may be achieved by any suitable method or configuration. For example, the layers 110, 112 may be in direct contact where at the interface some particle mixing may occur. Alternatively, a physical implement like a screen may be used to separate the layers 110, 112.

The layered catalyst bed 108 may be sized in the same or a similar manner to conventional catalyst beds. Typically, catalyst beds are cylindrical with a diameter of about 6 inches to about 200 inches, or about 6 inches to about 50 inches, or about 25 inches to about 100 inches, or about 75 inches to about 200 inches with corresponding inlet(s) and/or distribution implements for the feed stream 102 to ensure proper distribution and flow through the catalyst bed 108. One skilled in the art will recognize that there are several configurations for the catalyst bed 108 and feed stock distribution.

The light off time of a catalyst bed is the time that it takes for the catalyst bed to reach a self-sustaining, operating temperature. Herein, an electric heater is used to heat a portion of the catalyst bed. Reactants are flowed through the catalyst bed during preheating. Because the reaction is exothermic, the catalyst bed continues to heat. Once the average bed temperature reaches operating conditions, the electric heater is removed and the bed temperature is self-sustaining. The amount of time from when the electric heater reaches its set point temperature (e.g., 700° F. or 371° C.) to the time in which the average bed temperature reaches self-sustaining, operating temperature (e.g., 1000° F. or 537° C.) is the light off time.

The layered catalyst bed 108 may operate at an average bed temperature of about 500° C. to about 700° C., or about 500° C. to about 600° C., or about 550° C. to about 650° C., or about 600° C. to about 700° C. The layered catalyst bed 108 may have a light off time of about 0.1 hours to about 3 hours, or about 0.3 hours to about 2 hours, or about 0.5 hours to about 1 hour.

The layered catalyst bed 108 may operate at a pressure of about 0 psig to about 50 psig, or about 0 psig to about 20 psig, or about 15 psig to about 35 psig, or about 30 psig to about 50 psig.

The product stream 116 at the layered catalyst bed outlet may have a temperature of about 290° C. to about 700° C., or about 290° C. to about 500° C., or about 450° C. to about 700° C.

Silver Catalyst Particles

The first and second catalysts described herein are different and can be characterized by one or more of purity, surface area, x-ray diffraction pattern, weight average diameter, apparent bulk density, oxygen desorption temperature, and crystal morphology. While some ranges of properties may overlap, the values of the catalysts used should be different.

One or both of the first and second silver catalyst particles may be silver alloys. The silver may be alloyed with one or more alloy metals selected from the group consisting of: palladium, platinum, rhodium, ruthenium, and gold. The silver alloys can comprise 5 wt % to 80 wt % of the alloy metal and 20 wt % to 95 wt % silver.

For the silver catalysts described herein, purity is the weight percent of the silver and, when included, alloy metal in the silver catalyst. Purity is measured by digesting the silver catalyst and performing inductively coupled plasma-optical emission spectroscopy measurements.

The first silver catalyst particles may have a purity of about 98% to about 99.9%, or about 99% to about 99.5%, or about 99.5% to about 99.9%. For example, for a first silver catalyst not alloyed, the first silver catalyst may comprise silver at about 98 wt % to about 99.9 wt %, or about 99 wt % to about 99.5 wt %, or about 99.5 wt % to about 99.9 wt % of the first silver catalyst. In another example, for a first silver catalyst that is alloyed, the first silver catalyst may comprise silver and one or more alloy metals having a cumulative silver and alloy metal wt % at about 98% to about 99.9%, or about 99% to about 99.5%, or about 99.5% to about 99.9% of the first silver catalyst.

The second silver catalyst particles may have a purity of about 85% to about 99%, or about 85% to about 90%, or about 90% to about 95%. For example, for a second silver catalyst not alloyed, the second silver catalyst may comprise silver at about 98 wt % to about 99.9 wt %, or about 99 wt % to about 99.5 wt %, or about 99.5 wt % to about 99.9 wt % of the second silver catalyst. In another example, for a second silver catalyst that is alloyed, the second silver catalyst may comprise silver and one or more alloy metals having a cumulative silver and alloy metal wt % at about 98% to about 99.9%, or about 99% to about 99.5%, or about 99.5% to about 99.9% of the second silver catalyst.

Preferably, the purity of the first silver catalyst particles is greater than the purity of the second silver catalyst particles. For example, the first silver catalyst particles may have a purity of about 98% to about 99.9%, or about 99% to about 99.5%, or about 99.5% to about 99.9%, and the second silver catalyst particles may have a purity of about 85% to about 99%, or about 85% to about 90%, or about 90% to about 95%, where the purity of the first silver catalyst particles is greater than the purity of the second silver catalyst particles.

Surface area is measured by krypton adsorption according to ASTM D4780-12(2017)*el* where the sample is contained in a vessel that is submerged in liquid nitrogen.

The first silver catalyst particles may have a surface area of about 0.01 $m^2/g$ to about 0.02 $m^2/g$, or about 0.011 $m^2/g$ to about 0.018 $m^2/g$, or about 0.012 $m^2/g$ to about 0.016 $m^2/g$.

The second silver catalyst particles may have a surface area of about 0.001 $m^2/g$ to about 0.01 $m^2/g$, or about 0.002 $m^2/g$ to about 0.008 $m^2/g$, or about 0.003 $m^2/g$ to about 0.006 $m^2/g$.

Preferably, the first silver catalyst particles has a higher surface area than the second silver catalyst particles. Without being limited by theory, it is believed that the majority of the methanol is converted to formaldehyde by the first catalyst and the second catalyst provides additional catalysis, if needed, and heat transfer capabilities. Further, because the second silver catalyst particles is less reactive than the first silver catalyst particles, the side reactions are minimized, which produces a more pure formaldehyde product.

For example, the first silver catalyst particles may have a surface area of about 0.01 $m^2/g$ to about 0.02 $m^2/g$, and the second silver catalyst particles may have a surface area of about 0.001 $m^2/g$ to about 0.01 $m^2/g$, where the first silver catalyst particles has a higher surface area than the second silver catalyst particles.

X-ray diffraction patterns are measured with a Cu K-alpha source for 2 theta angle between 30 degrees and 120 degrees for characteristic silver as described in the International Center for Diffraction Data (ICDD) database.

The first silver catalyst particles may have an x-ray diffraction pattern characterized by having a (1 1 1) Miller index intensity greater than an intensity of each of the following Miller indices: (2 0 0), (2 2 0), (3 1 1), (2 2 2), (4 0 0), (3 3 1), (4 2 0), and (1 1 0). Further, the x-ray diffraction pattern of the first silver catalyst particles may be characterized by having a (1 1 1):(2 2 0) Miller indices intensity ratio of about 1:1 to about 3.5:1, or about 1.5:1 to about 3:1, or about 1.5:1 to about 2.5:1, or about 2:1 to about 3:1. Further, the x-ray diffraction pattern of the first silver catalyst particles may be characterized by having a (1 1 1):(1 1 0) Miller indices intensity ratio of about 1.5:1 or greater, or about 1.5:1 to about 100:1 or greater, or about 5:1 to about 25:1, or about 20:1 to about 60:1, or about 40:1 to about 80:1, or about 60:1 to about 100:1 or greater. The x-ray diffraction pattern of the first silver catalyst particles may be characterized by one or more of the foregoing characterizations. For example, the x-ray diffraction pattern of the first silver catalyst particles may be characterized by having a (1 1 1) Miller index intensity greater than an intensity of each of the following Miller indices: (2 0 0), (2 2 0), (3 1 1), (2 2 2), (4 0 0), (3 3 1), (4 2 0), and (1 1 0) and by having a (1 1 1):(2 2 0) Miller indices intensity ratio of about 1:1 to about 3.5:1, or about 1.5:1 to about 3:1, or about 1.5:1 to about 2.5:1, or about 2:1 to about 3:1. In another example, the foregoing x-ray diffraction pattern may also be characterized by having a (1 1 1):(1 1 0) Miller indices intensity ratio of about 1.5:1 or greater, or about 1.5:1 to about 100:1 or greater, or about 5:1 to about 25:1, or about 20:1 to about 60:1, or about 40:1 to about 80:1, or about 60:1 to about 100:1 or greater.

The second silver catalyst particles may have an x-ray diffraction pattern characterized by having a (1 1 1) Miller index intensity less than an intensity of one or more of the following Miller indices: (2 0 0), (2 2 0), (3 1 1), (2 2 2), (4 0 0), (3 3 1), (4 2 0), and (1 1 0). Further, the second silver catalyst particles may have an x-ray diffraction pattern characterized by having ratio of the (1 1 1) Miller index intensity to the intensity of largest intensity peak in the 2 theta angle between 30 degrees and 120 degrees range of 0.7 or less, or 0.6 or less, or 0.5 or less. Further, the x-ray diffraction pattern of the second silver catalyst particles may be characterized by having a (1 1 1):(2 2 0) Miller indices intensity ratio of about 0.05:1 to about 0.8:1, or about 0.1:1 to about 0.6:1, or about 0.2:1 to about 0.4:1. The x-ray diffraction pattern of the second silver catalyst particles may be characterized by one or both of the foregoing characterizations.

The silver catalyst particles are sieved as described in ASTM D4513-11(2017).

The first silver catalyst particles may be sieved with the small diameter sieve being about 0.25 mm to about 1 mm and the large diameter sieve being 1 mm to about 4 mm, wherein the small diameter sieve is less than the large diameter sieve. For example, the first silver catalyst particles may be sieved to have sieved particle sizes ranging from about 0.25 mm to about 4 mm, or from about 0.5 mm to about 1 mm.

The second silver catalyst particles may be sieved with the small diameter sieve being about 0.5 mm to about 1 mm and the large diameter sieve being 1 mm to about 4 mm, wherein the small diameter sieve is less than the large diameter sieve. For example, the second silver catalyst particles may be sieved to have sieved particle sizes ranging from about 0.5 mm to about 4 mm, or from about 1 mm to about 2.5 mm.

Preferably, the first silver catalyst particles are sieved to include particles smaller than included in the second silver catalyst particles. For example, the first silver catalyst particles may be sieved to have sieved particle sizes ranging from about 0.25 mm to about 4 mm, and the second silver catalyst particles may be sieved to have sieved particle sizes ranging from about 0.5 mm to about 4 mm, wherein the first silver catalyst particles are sieved to include particles smaller than included in the second silver catalyst particles. In another example, the first silver catalyst particles may be sieved to have sieved particle sizes ranging from about 0.5 mm to about 1 mm, and the second silver catalyst particles may be sieved to have sieved particles size ranging from about 1 mm to about 2.5 mm, wherein the first silver catalyst particles are sieved to include particles smaller than included in the second silver catalyst particles.

Apparent bulk density is measured by ASTM D4180-13 (2018) regardless of particle size.

The first silver catalyst particles may have an apparent bulk density of about 3 g/mL or less, or about 1 g/mL to about 3 g/mL, or about 2 g/mL to about 3 g/mL, or about 2.2 g/mL to about 2.7 g/mL.

The second silver catalyst particles may have an apparent bulk density of about 3 g/mL or greater, or about 3 g/mL to about 5 g/mL, or about 3 g/mL to about 4 g/mL, or about 3.4 g/mL to about 4 g/mL.

Preferably, the apparent bulk density of the first silver catalyst particles is less than the apparent bulk density of the second silver catalyst particles. Without being limited by theory it is believed that a higher apparent bulk density for the second silver catalyst particles improves the heat transfer properties of the second layer.

Temperature programmed desorption (TPD) analysis determine the number, type, and strength of molecules on a catalyst at various temperatures. Oxygen desorption temperature is a measure of the activation barrier of redox sites on silver catalysts where lower temperature indicates a lower activation barrier and a higher reactivity. Oxygen desorption temperature is measured by standard TPD methods that include using Micromeritics AutoChem II 2920 to increase the temperature at 10° C./min to 600° C. under an argon flow.

The first silver catalyst particles may have an oxygen desorption temperature of about 220° C. to about 270° C., or about 235° C. to about 260° C.

The second silver catalyst particles may have an oxygen desorption temperature of about 270° C. to about 310° C., or about 280° C. to about 300° C.

Preferably, the oxygen desorption temperature of the first silver catalyst particles is less than the oxygen desorption temperature of the second silver catalyst particles. For example, the first silver catalyst particles may have an oxygen desorption temperature of about 220° C. to about 270° C., or about 235° C. to about 260° C., and the second silver catalyst particles may have an oxygen desorption temperature of about 270° C. to about 310° C., or about 280° C. to about 300° C., where the oxygen desorption temperature of the first silver catalyst particles is less than the oxygen desorption temperature of the second silver catalyst particles.

Crystal morphology is determined by visual inspection in a scanning electron microscope. Generally, the first silver catalyst has a higher crystallinity, which manifests as more facets and crystal faces. For example, the first silver catalyst particles may have a crystal morphology that is dendritic (e.g., like a tree) as compared to the second silver catalyst particles, which may have less definable morphology that are more irregular and rounded with fewer facets.

Example Embodiments

A nonlimiting example embodiment of the present disclosure is a method comprising: passing a feed stream comprising methanol and oxygen through a layered catalyst bed having a first layer comprising a first silver catalyst particles and a second layer comprising a second silver catalyst particles that are different than the first silver catalyst particles, wherein the feed stream passes through the first layer before the second layer, wherein the first silver catalyst particles has a greater reaction activity for converting methanol and oxygen to formaldehyde; and reacting the methanol and the oxygen in the presence of the catalysts to produce a product stream comprising formaldehyde. Additional embodiments may include one or more of the following: Element 1: the method further comprising: cooling and purifying the product stream; Element 2: wherein the first silver catalyst particles has a purity of about 98% to about 99.5%, and wherein the second silver catalyst particles has a purity of about 85% to about 99%, where the purity of the first silver catalyst particles is greater than the purity of the second silver catalyst particles; Element 3: wherein one or both of the first and second silver catalyst particles comprises about 5 wt % to about 80 wt % of one or more alloy metals and about 20 wt % to about 95 wt % silver; Element 4: Element 3 and wherein the one or more alloy metals is selected from the group consisting of: palladium, platinum, rhodium, ruthenium, and gold; Element 5: wherein the first silver catalyst particles have sieved particle sizes ranging from about 0.25 mm to about 4 mm, and the second silver catalyst particles have sieved particle sizes ranging from about 0.5 mm to about 4 mm, wherein the first silver catalyst particles are sieved to include particles smaller than included in the second silver catalyst particles; Element 6: wherein the first silver catalyst particles have an apparent bulk density of about 3 g/mL or less, wherein the second silver catalyst particles have an apparent bulk density of about 3 g/mL or greater, and wherein the apparent bulk density of the first silver catalyst particles is smaller than the apparent bulk density of the second silver catalyst particles; Element 7: wherein the first silver catalyst particles have an oxygen desorption temperature of about 220° C. to about 270° C., wherein the second silver catalyst particles have an oxygen desorption temperature of about 270° C. to about 310° C., and wherein the oxygen desorption temperature of the first silver catalyst particles is smaller than the oxygen desorption temperature of the second silver catalyst particles; Element 8: wherein the first silver catalyst particles have a dendritic morphology; Element 9: wherein the first silver catalyst particles have an x-ray diffraction pattern characterized by having a (1 1 1) Miller index intensity greater than an intensity of each of the following Miller indices: (2 0 0), (2 2 0), (3 1 1), (2 2 2), (4 0 0), (3 3 1), (4 2 0), and (1 1 0); Element 10: wherein the first silver catalyst particles have an x-ray diffraction pattern characterized by having a (1 1 1):(2 2 0) Miller indices intensity ratio of about 1:1 to about 3.5:1; Element 11: wherein the first silver catalyst particles have an x-ray diffraction pattern characterized by having a (1 1 1):(1 1 0) Miller indices intensity ratio of about 1.5:1 or greater; Element 12: wherein the second silver catalyst particles have an x-ray diffraction pattern characterized by having a (1 1 1) Miller index intensity less than an intensity of one or more of the following Miller indices: (2 0 0), (2 2 0), (3 1 1), (2 2 2), (4 0 0), (3 3 1), (4 2 0), and (1 1 0); Element 13: wherein the second silver catalyst particles have an x-ray diffraction pattern characterized by having ratio of a (1 1 1) Miller index intensity to an intensity of a largest intensity peak between 30 degrees 2 theta angle and 120 degrees range 2 theta angle of 0.7 or less; Element 14: wherein the second silver catalyst particles have an x-ray diffraction pattern characterized by having a (1 1 1):(2 2 0) Miller indices ratio of about 0.05:1 to about 0.8:1; Element 15: wherein a weight ratio of the first layer to the second layer is about 0.01:1 to about 0.5:1; Element 16: wherein the feed stream has a temperature of 90° C. to 170° C.; Element 17: wherein the feed stream comprises, by volume, about 15% to about 43% methanol, about 5% to about 15% oxygen, about 35% to about 50% inert gas, 0% to 30% formaldehyde, and about 9% to about 30% water; Element 18: wherein the layered catalyst bed has an average bed temperature of 500° C. to 700° C.; Element 19: wherein the layered catalyst bed has a pressure of about 0 psig to about 50 psig; Element 20: wherein the layered catalyst bed has a light off time of about 0.1 hours to about 3 hours; and Element 21: wherein the product stream has a temperature of 290° C. to 700° C. For each of the foregoing where a range is presented, the range encompasses subset ranges including, but not limited to, the subset ranges described herein. Examples of combinations in various embodiments may include, but are not limited to, Element 2 in combination with Element 3 and optionally Element 4; two or more of Elements 5-7 in combination; two or more of Elements 9-11 in combination; two or more of Elements 12-14 in combination; one or more of Elements 5-7 in combination with one or more of Elements 9-11 in combination and optionally in further combination with one or more of Elements 12-14; one or more of Elements 5-7 in combination with one or more of Elements 12-14; one or more of Elements 9-11 in combination with one or more of Elements 12-14; Element 8 in combination with one or more of Elements 5-7 and/or in combination with one or more of Elements 9-11 and/or in combination with one or more of Elements 12-14; Element 2 (optionally in combination with Element 3) and/or Element 4 in combination with one or more of Elements 5-7 and/or in combination with one or more of Elements 9-11 and/or in combination with one or more of Elements 12-14; Element 2 (optionally in combination with Element 3) and/or Element 4 in combination with Element 8; two or more of Elements 15-21 in combination; one or more of Elements 15-21 in combination with one or more of Elements 2-14 including, but not limited to, in the foregoing combinations; and Element 1 in combination with one or more of Elements 2-21 including, but not limited to, in the foregoing combinations.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Figure 2A:
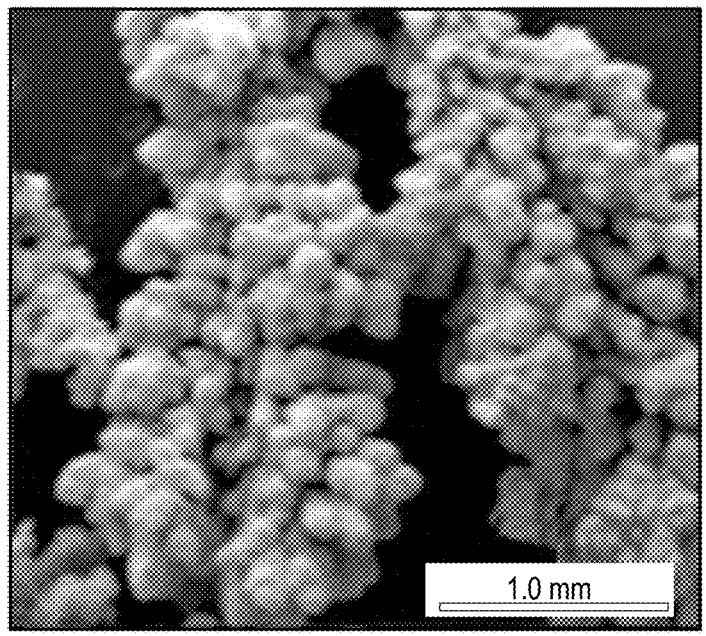
FIGS. 2A-2B are SEM micrographs of Silver Catalyst A.
Figure 2B:
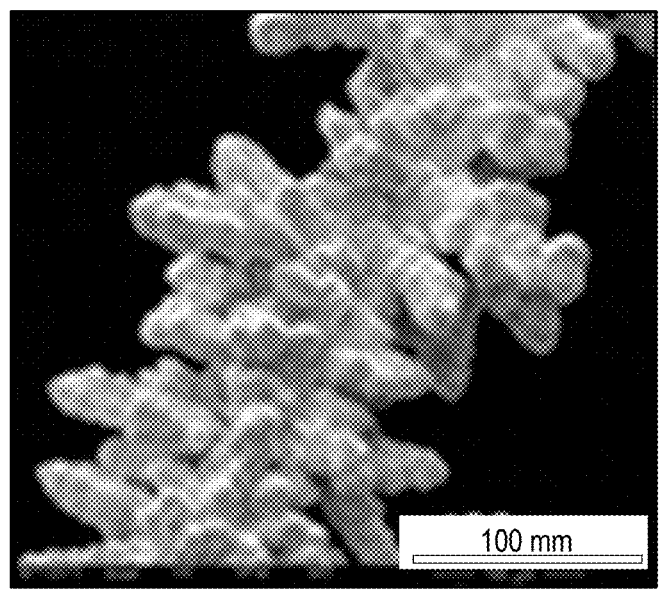
Figure 3:
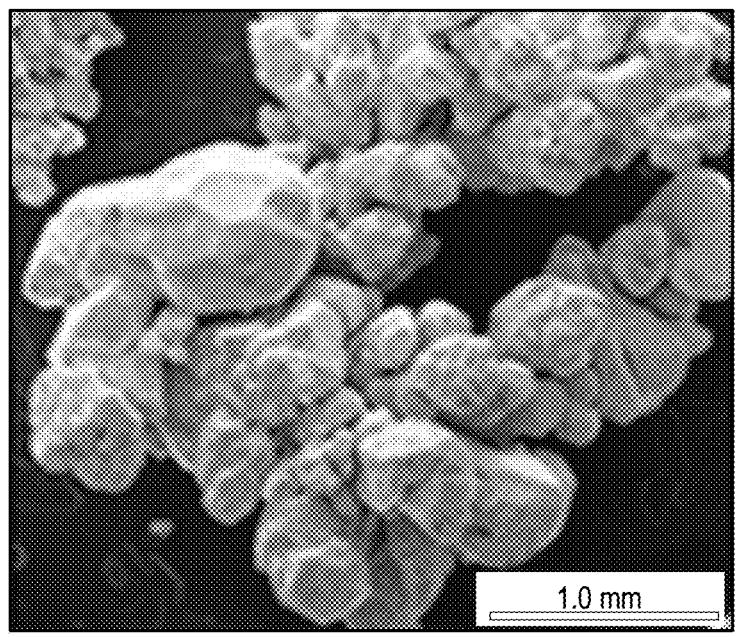
FIG. 3 is a SEM micrograph of Silver Catalyst B.

Silver Catalyst A and Silver Catalyst B were used to make catalyst beds. The XRD patterns for Silver Catalyst A and Silver Catalyst B are provided in Tables 1 and 2, respectively, and the properties of Silver Catalyst A and Silver Catalyst B are provided in Table 3. SEM micrographs of Silver Catalyst A showing a dendritic morphology and Silver Catalyst B showing an irregular and rounded morphology with fewer facets are provided in FIGS. 2A-2B and FIG. 3, respectively.

TABLE 1

| 2θ (°) | d (Å) | I/I$_O$ | (h k l) |
|---|---|---|---|
| 38.36 | 2.34 | 1.00 | (1 1 1) |
| 44.58 | 2.03 | 0.54 | (2 0 0) |
| 64.70 | 1.44 | 0.50 | (2 2 0) |
| 77.53 | 1.23 | 0.53 | (3 1 1) |
| 81.80 | 1.18 | 0.22 | (2 2 2) |
| 98.06 | 1.02 | 0.09 | (4 0 0) |
| 110.64 | 0.94 | 0.51 | (3 3 1) |
| 115.08 | 0.91 | 0.36 | (4 2 0) |

θ is the Bragg angle.
d is the interplanar spacing.
I$_O$ is the intensity of the strongest peak.
(h k l) is the Miller index.

TABLE 2

| 2θ (°) | d (Å) | I/I$_O$ | (h k l) |
|---|---|---|---|
| 38.41 | 2.34 | 0.26 | (1 1 1) |
| 44.58 | 2.03 | 0.26 | (2 0 0) |
| 64.69 | 1.44 | 1.00 | (2 2 0) |
| 44.72 | 1.23 | 0.25 | (3 1 1) |
| 81.64 | 1.18 | 0.17 | (2 2 2) |
| 98.05 | 1.02 | 0.04 | (4 0 0) |
| 110.58 | 0.94 | 0.26 | (3 3 1) |
| 115.02 | 0.91 | 0.48 | (4 2 0) |

TABLE 3

| Property | Silver Catalyst A | Silver Catalyst B |
|---|---|---|
| BET surface area (m$^2$/g) | 0.0141 | 0.0040 |
| Apparent bulk density (g/mL) | 2.45 | 3.78 |
| (1 1 1):(2 2 0) Miller indices intensity ratio | 2.00 | 0.26 |
| Oxygen desorption temp. (° C.) | 250 | 290 |
| Crystal morphology | coral, dendritic | spherical |

Two catalyst beds were prepared: Catalyst Bed 1 was a first layer of Silver Catalyst A, a second layer of Silver Catalyst B, and a weight ratio of the first layer to the second layer of 2 to 8; and Catalyst Bed 2 consisted of Silver Catalyst B. In a two-stage reactor using the same catalyst bed for the first and second stages, the catalyst beds were initially heated using electric heaters. Once achieving an average catalyst bed temperature of 1000° F. (538° C.), the electric heaters were removed and the light off time was determined. Catalyst Bed 1 had a light off time of 0.6 hours with an average bed temperature at light off time of 1080° F. (582° C.). Catalyst Bed 2 had a light off time of 10 hours with an average bed temperature at light off time of 1137° F. (614° C.). Further, Catalyst Bed 1 produced ⅓ less formic acid as compared to Catalyst Bed 2, which indicates less formaldehyde decomposition in Catalyst Bed 1. Additionally, Catalyst Bed 1 had twice the lifetime as compared to Catalyst Bed 2. This example illustrates that the layered catalyst beds of the present disclosure allow for a faster light off time and a lower overall bed temperature, which reduces fouling.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
passing a feed stream comprising methanol and oxygen through a layered catalyst bed having a first layer comprising a first silver catalyst particles and a second layer comprising a second silver catalyst particles that are different than the first silver catalyst particles, wherein the feed stream passes through the first layer before the second layer, wherein the first silver catalyst particles has a greater reaction activity for converting methanol and oxygen to formaldehyde, and wherein the first silver catalyst particles have sieved particle sizes ranging from about 0.25 mm to about 4 mm; and
reacting the methanol and the oxygen in the presence of the catalysts to produce a product stream comprising formaldehyde.

2. The method of claim 1 further comprising:
cooling and purifying the product stream.

3. The method of claim 1, wherein the first silver catalyst particles has a purity of about 98% to about 99.5%, and wherein the second silver catalyst particles has a purity of about 85% to about 99%, where the purity of the first silver catalyst particles is greater than the purity of the second silver catalyst particles.

4. The method of claim 1, wherein one or both of the first and second silver catalyst particles comprises about 5 wt % to about 80 wt % of one or more alloy metals and about 20 wt % to about 95 wt % silver.

5. The method of claim 4, wherein the one or more alloy metals is selected from the group consisting of: palladium, platinum, rhodium, ruthenium, and gold.

6. The method of claim 1, wherein the second silver catalyst particles have sieved particle sizes ranging from about 0.5 mm to about 4 mm, and wherein the first silver catalyst particles are sieved to include particles smaller than included in the second silver catalyst particles.

7. The method of claim 1, wherein the first silver catalyst particles have an apparent bulk density of about 3 g/mL or less, wherein the second silver catalyst particles have an apparent bulk density of about 3 g/mL or greater, and wherein the apparent bulk density of the first silver catalyst particles is smaller than the apparent bulk density of the second silver catalyst particles.

8. The method of claim 1, wherein the first silver catalyst particles have an oxygen desorption temperature of about 220° C. to about 270° C., wherein the second silver catalyst particles have an oxygen desorption temperature of about 270° C. to about 310° C., and wherein the oxygen desorption temperature of the first silver catalyst particles is smaller than the oxygen desorption temperature of the second silver catalyst particles.

9. The method of claim 1, wherein the first silver catalyst particles have a dendritic morphology.

10. The method of claim 1, wherein the first silver catalyst particles have an x-ray diffraction pattern characterized by having a (1 1 1) Miller index intensity greater than an intensity of each of the following Miller indices: (2 0 0), (2 2 0), (3 1 1), (2 2 2), (4 0 0), (3 3 1), (420), and (1 1 0).

11. The method of claim 1, wherein the first silver catalyst particles have an x-ray diffraction pattern characterized by having a (1 1 1): (2 2 0) Miller indices intensity ratio of about 1:1 to about 3.5:1.

12. The method of claim 1, wherein the first silver catalyst particles have an x-ray diffraction pattern characterized by having a (1 1 1): (1 1 0) Miller indices intensity ratio of about 1.5:1 or greater.

13. The method of claim 1, wherein the second silver catalyst particles have an x-ray diffraction pattern characterized by having a (1 1 1) Miller index intensity less than an intensity of one or more of the following Miller indices: (2 0 0), (2 2 0), (3 1 1), (2 2 2), (400), (3 3 1), (4 2 0), and (1 1 0).

14. The method of claim 1, wherein the second silver catalyst particles have an x-ray diffraction pattern characterized by having ratio of a (1 1 1) Miller index intensity to an intensity of a largest intensity peak between 30 degrees 2 theta angle and 120 degrees range 2 theta angle of 0.7 or less.

15. The method of claim 1, wherein the second silver catalyst particles have an x-ray diffraction pattern characterized by having a (1 1 1): (2 2 0) Miller indices ratio of about 0.05:1 to about 0.8:1.

16. The method of claim 1, wherein a weight ratio of the first layer to the second layer is about 0.01:1 to about 0.5:1.

17. The method of claim 1, wherein the feed stream has a temperature of 90° C. to 170° C.

18. The method of claim 1, wherein the layered catalyst bed has an average bed temperature of 500° C. to 700° C.

19. The method of claim 1, wherein the layered catalyst bed has a pressure of about 0 psig to about 50 psig.

20. The method of claim 1, wherein the layered catalyst bed has a light off time of about 0.1 hours to about 3 hours.

21. The method of claim 1, wherein the product stream has a temperature of 290° C. to 700° C.

22. The method of claim 1, wherein the feed stream comprises, by volume, about 15% to about 43% methanol, about 5% to about 15% oxygen, about 35% to about 50% inert gas, 0% to 30% formaldehyde, and about 9% to about 30% water.

23. The method of claim 1, wherein the first silver catalyst particles have a surface area of about 0.01 $m^2/g$ to about 0.02 $m^2/g$.

* * * * *